United States Patent [19]

Greene et al.

[11] Patent Number: 4,552,967

[45] Date of Patent: Nov. 12, 1985

[54] PROCESS FOR THE SYNTHESIS OF INTERMEDIATES IN THE PREPARATION OF DIAMINOPYRIDINES

[75] Inventors: James M. Greene; Edward R. Lavagnino; Andrew J. Pike, all of Indianapolis, Ind.; Edward C. Taylor, Princeton, N.J.

[73] Assignee: Eli Lilly and Company, Indianapolis, Ind.

[21] Appl. No.: 570,144

[22] Filed: Jan. 12, 1984

[51] Int. Cl.[4] ..................... C07D 213/61; C07B 29/00
[52] U.S. Cl. .................................................... 546/307
[58] Field of Search ......................................... 546/307

[56] References Cited

U.S. PATENT DOCUMENTS 3,278,604 10/1966 Hoffman ............................. 564/399

FOREIGN PATENT DOCUMENTS 169688  6/1922  United Kingdom .

OTHER PUBLICATIONS

Streitweiser et al., "Introduction to Organic Chemistry", (1976), pp. 966, 1101, 1102.
*Organic Syntheses, Collective* vol. 2, 221-222.
Koenigs et al., in *Berichte* 57, 1187 (1924).
Clark-Lewis et al., in *J. Chem. Soc.* 2379 (1962), "Preparation of 3,4-Diamino-, 3-Amino-4-Methylamino-, and 4-Amino-3-Methylamino-Pyridine".

*Primary Examiner*—Henry R. Jiles
*Assistant Examiner*—Dale A. Bjorkman
*Attorney, Agent, or Firm*—Bruce J. Barclay; Leroy Whitaker; Arthur R. Whale

[57] ABSTRACT

The present invention relates to a process for preparing aminonitropyridines comprising reacting an alkoxynitropyridine with ammonium acetate.

12 Claims, No Drawings

PROCESS FOR THE SYNTHESIS OF INTERMEDIATES IN THE PREPARATION OF DIAMINOPYRIDINES

SUMMARY OF THE INVENTION

The present invention relates to a process for preparing an aminonitropyridine of the formula

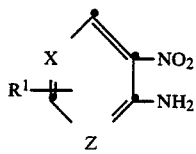

wherein $R^1$ is hydrogen or $C_1-C_4$ alkyl and one of X and Z is CH and the other is N, comprising reacting an alkoxynitropyridine of the formula

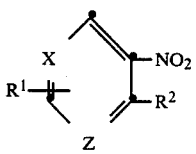

or a salt thereof, wherein $R^2$ is $C_1-C_4$ alkoxy, with ammonium acetate at a temperature in the range of from about 50° C. to about 150° C.

DETAILED DESCRIPTION OF THE INVENTION

In the above formula, $C_1-C_4$ alkyl represents a straight or branched alkyl chain having from one to four carbon atoms. Typical $C_1-C_4$ alkyl groups include methyl, ethyl, n-propyl, isopropyl, n-butyl, isobutyl, sec.-butyl and t-butyl.

$C_1-C_4$ Alkoxy represents a straight or branched alkoxy chain having from one to four carbon atoms. Typical $C_1-C_4$ alkoxy groups include methoxy, ethoxy, n-propoxy, isopropoxy, n-butoxy, isobutoxy and the like.

While the entire scope of process variables taught herein are believed operable, the present process does have preferred aspects. In the above formulas, preferably $R^1$ is hydrogen, $R^2$ is methoxy and especially ethoxy and X is N and Z is CH. Other preferred process conditions will be noted hereinafter.

The process of the present invention is generally conducted as follows. Approximately one equivalent of an alkoxynitropyridine, or a salt thereof, is combined with at least one equivalent of ammonium acetate in a suitable reaction flask. Alkoxynitropyridine salts comprehended as starting materials for the present process include acid addition salts, such as hydrochlorides, hydroiodides, hydrobromides, and the like. The amount of ammonium acetate in excess of one equivalent of the starting pyridine is not critical but typically approximately from three to ten equivalents of ammonium acetate are employed in the present process.

The present process may be conducted in a suitable solvent if desired, but may also be carried out neat. When a solvent is employed, suitable solvents include the protic solvents such as the alcohols, for example methanol or ethanol, acetic acid or especially water. The concentration of the starting pyridine in the solvent is not critical, but it is preferred to employ a sufficient amount of solvent to keep the starting pyridine in solution, or a slight excess. Large volumes of solvent are not necessary or desirable in this process.

The process of the present invention is substantially complete after about 30 minutes to 24 hours when conducted at a temperature in the range of from about 50° C. to about 150° C., more preferably from about 75° C. to about 135° C. In particular, when a solvent is employed in the present process, the preferred reaction temperature is the reflux temperature of the reaction mixture. Once the process of the present invention is complete, the product may be isolated according to standard procedures. When no solvent is employed in the process, the product is typically isolated by pouring the reaction mixture into water and collecting the precipitated solid by filtration or extracting the aqueous phase with a water immiscible organic solvent such as dichloromethane or ethyl acetate. The organic solvent may then be evaporated under reduced pressure to isolate the residual product. When a solvent is employed in the present process, the reaction mixture is made basic with a suitable base such as ammonium hydroxide, for example, and the precipitated product is collected by filtration. The product thus isolated is then typically dried under vacuum and may be further purified if desired by standard procedures such as crystallization from common solvents or purification over solid supports such as silica gel or alumina.

The present process has been found to produce large quantities of either a 2- or 4-amino-3-nitropyridine in very high yields and to provide the product consistently in high purity, so that the compound may be used in the preparation of biologically active compounds without additional expensive purification steps. The use of an alkoxypyridine in the present process has an added advantage over the use of a chloropyridine in that the latter compound is a lachrymator, irritant and skin sensitizer and would accordingly be hazardous to use in large scale industrial processes.

The aminonitropyridine compounds prepared by the present process are preferably used to prepare the corresponding diaminopyridine derivatives. The diaminopyridine is in turn useful as an intermediate in the synthesis of a variety of compounds, for example pharmaceuticals useful for the treatment of a variety of human disorders. See, e.g. U.S. Pat. Nos. 3,985,891 and 4,327,100 (use of 2,3-diaminopyridine in the preparation of imidazo[4,5-b]pyridine inotropic agents); and U.S. application Ser. No. 469,883, now abandoned, and European Patent Application No. 72,926 (use of 3,4-diaminopyridine in the preparation of imidazo[4,5-c]pyridine inotropic agents).

The aminonitropyridines prepared by the process of the present invention are reduced to the corresponding diaminopyridines according to procedures well known to those skilled in the art. This reduction is typically carried out in a suitable solvent and in the presence of an appropriate reducing agent. Any number of reducing agents may be employed in this synthesis. See e.g., Clark-Lewis et al. in *J. Chem. Soc.* 442 (1957) where 3-amino-2-nitropyridine is reduced to the corresponding 2,3-diaminopyridine with hydrogen and Raney nickel catalyst. However, the present reduction is preferably conducted with a palladium on carbon catalyst. Typically the reaction is conducted in an alcoholic solvent such as methanol or ethanol in the presence of from about 20% to 50% of catalyst by weight and in the presence of hydrogen gas. The product is isolated by filtering the reaction mixture through infusorial earth and evaporating the filtrate to dryness under reduced pressure.

The alkoxynitropyridine starting materials employed in the present process are readily prepared by a variety of known reactions from assorted readily available starting materials. These reactions are represented by the following scheme:

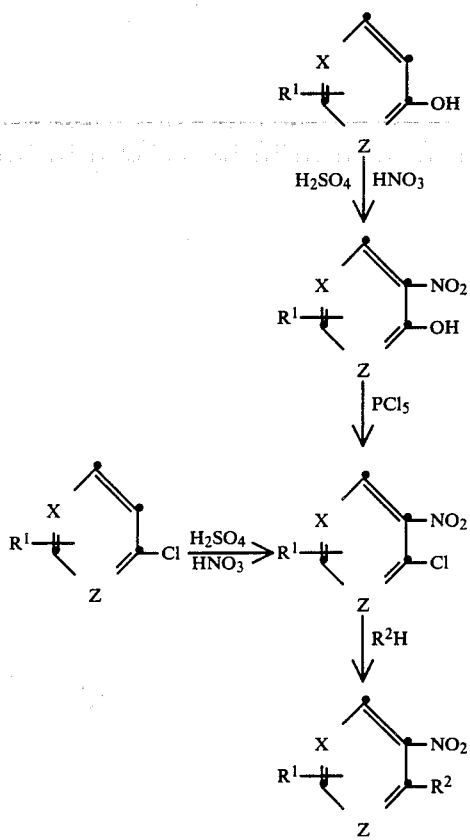

wherein $R^1$, $R^2$, X and Z are as defined above.

The hydroxypyridine and chloropyridine starting materials are generally commercially available but are also readily prepared by well known procedures. The processes for converting those compounds to the corresponding nitropyridine derivatives with nitric acid and sulfuric acid are reported in the literature as well. See, e.g. Koenigs and Freter, *Ber.* 57, 1187 (1924). Converting the hydroxynitropyridine to the chloronitropyridine is also readily accomplished by reacting the hydroxy compound with either phosphorus pentachloride or phosphorus oxychloride. See Koenings et al., supra.

The alkoxynitropyridine derivatives used as starting materials in the present process are conveniently prepared by stirring a solution of the chloronitropyridine in a suitable alcohol at a temperature in the range of 20° C. to 150° C., more preferably at the reflux temperature of the reaction mixture. The reaction is substantially complete after about 30 minutes to 24 hours when conducted at a temperature in the range specified. The product may be isolated by standard procedures if desired.

The process of the present invention is further illustrated by the following Examples. The Examples are not intended to be limiting in any respect and should not be so construed.

EXAMPLE 1

Preparation of 3-Nitro-4-aminopyridine

A 500 ml 3-neck round bottom flask equipped with a condenser, thermometer and mechanical stirrer was charged with 78.4 g (0.383 mol) of 4-ethoxy-3-nitropyridine hydrochloride, 118.1 g (1.53 mol) of ammonium acetate and 183 ml of water. The stirred reaction mixture was refluxed for 7½ hours and the progress of the reaction was followed by thin layer chromatography employing a 10:1 ethyl acetate:triethylamine solvent system. The reaction flask was chilled to approximately 4° C. after the pH of the mixture was adjusted from 5.2 to 8.1 with 60 ml of concentrated ammonium hydroxide. The yellow precipitate was collected by filtration, washed twice with chilled water and dried under vacuum at 50° C. for 10 hours. A total dry weight of 46.15 g (86.6% yield) of 3-nitro-4-aminopyridine was obtained. The product was verified by NMR and compared to an authentic sample.

Analysis calculated for $C_5H_5N_3O_2$:
Theory: C, 43.17; H, 3.62; N, 30.21;
Found : C, 42.93; H, 3.81; N, 29.97.

EXAMPLE 2

Preparation of 3-Nitro-4-aminopyridine

A 25 ml round bottom flask was fitted with a reflux condenser and magnetic stirrer and placed in an oil bath. The flask was charged with 1.0 g (5.95 mmol) of 4-ethoxy-3-nitropyridine and 5.0 g (65 mmol) of ammonium acetate. The reaction mixture was heated at 120° C. to provide a homogeneous liquid. The progress of the reaction was followed by thin layer chromotography employing a 10:1 ethyl acetate:triethylamine solvent system. After 2½ hours the reaction mixture was cooled and poured into water. The yellow precipitate was collected by filtration, washed with water and dried in vacuo at 60° C. over phosphorus pentoxide. A total of 620 mg of 3-nitro-4-aminopyridine was obtained and chromatographically verified by comparison to an authentic reference standard. Yield 75%.

EXAMPLE 3

Preparation of 3-Nitro-4-aminopyridine

A 22 liter 4-neck flask fitted with a reflux condenser, thermometer and mechanical stirrer was charged with 1300 g (6.35 mol) of 4-ethoxy-3-nitropyridine hydrochloride, 2438 g (31.62 mol) of ammonium acetate and 13 l. of glacial acetic acid. The reaction mixture was refluxed for 3 hours and cooled. The volatiles were evaporated under reduced pressure and the residue was dissolved in 1N hydrochloric acid. The insoluble material was removed by filtration and the pH of the filtrate was adjusted to approximately 8.5 with concentrated ammonium hydroxide. The precipitated solid was collected by filtration, washed with water and dried in a forced air oven to provide 701 g of 3-nitro-4-aminopyridine. Yield 79.3%. mp=187°–195° C. The identity of the product was also confirmed by chromatography in a 10:1 ethyl acetate:triethylamine solvent system by comparison to a reference standard.

EXAMPLE 4

Preparation of 3-Nitro-4-aminopyridine

A 50 ml 3-neck round bottom flask fitted with a condenser, thermometer, and mechanical stirrer was charged with 3.0 g (14.66 mmol) of 4-ethoxy-3-nitropyridine hydrochloride, 6.1 g (79.9 mmol) of ammonium acetate and 6.7 ml of absolute ethanol. The reaction mixture was refluxed for approximately 24 hours and cooled to about 4° C. The pH of the solution was adjusted to 8.0 with base and the precipitated solid was collected by filtration. The product was rinsed with chilled ethanol and dried in vacuo at 50° C. to afford 2.41 g of 3-nitro-4-aminopyridine (and a small amount of ammonium acetate). The identity of the product was verified by NMR comparison to an authentic sample.

EXAMPLE 5

Preparation of 3-Nitro-2-aminopyridine

One gram (6.5 mmol) of 2-methoxy-3-nitropyridine and 5.0 g (65 mmol) of ammonium acetate were added to a 100 ml round bottom flask. The reaction mixture was heated at 150° C. for approximately 16 hours under an argon atmosphere. An additional 5 g of ammonium acetate was added to the reaction mixture which was allowed to heat for an additional 8 hours. Thin layer chromatography of the mixture indicated that both product and starting material were present. The reaction mixture was cooled and poured into approximately 100 ml of water. The precipitated solid was collected by filtration to provide 209.8 mg of 3-nitro-2-aminopyridine. m/e 139. The NMR spectrum of the collected product was identical to that of an authentic reference standard.

Analysis calculated for $C_5H_5N_3O_2$:
Theory: C, 43.17; H, 3.62; N, 30.21;
Found: C, 42.89; H, 3.38; N, 30.23.

An additional 105.7 mg of unpurified 3-nitro-2-aminopyridine was subsequently isolated from the filtrate to afford a total yield of 315.5 mg of product. Yield 35%.

We claim:

1. A process for preparing an aminonitropyridine of the formula

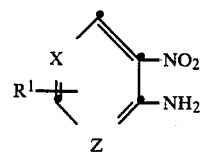

wherein $R^1$ is hydrogen or $C_1$–$C_4$ alkyl and one of X and Z is CH and the other is N, comprising reacting an alkoxynitropyridine of the formula

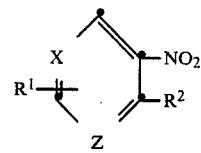

or a salt thereof, wherein $R^2$ is $C_1$–$C_4$ alkoxy, with ammonium acetate at a temperature in the range of from about 50° C. to about 150° C.

2. A process of claim 1 wherein $R^1$ is hydrogen.
3. A process of claim 2 wherein X is N and Z is CH.
4. A process of claim 3 wherein $R^2$ is ethoxy.
5. A process of claim 3 wherein $R^2$ is methoxy.
6. A process of claim 3 wherein a suitable solvent is employed in the reaction mixture.
7. A process of claim 6 wherein the solvent is water.
8. A process of claim 2 wherein X is CH and Z is N.
9. A process of claim 8 wherein $R^2$ is ethoxy.
10. A process of claim 8 wherein $R^2$ is methoxy.
11. A process of claim 8 wherein a suitable solvent is employed in the reaction mixture.
12. A process of claim 11 wherein the solvent is water.

* * * * *